US00PP24154P2

(12) United States Plant Patent
Bentley

(10) Patent No.: US PP24,154 P2
(45) Date of Patent: Jan. 7, 2014

(54) ***SALVIA* PLANT NAMED 'EGGBEN004'**

(50) Latin Name: *Salvia microphylla×greggii*
Varietal Denomination: EGGBEN004

(76) Inventor: Howard Bentley, Wonga Park (AU)

( * ) Notice: Subject to any disclaimer, the term of this patent is extended or adjusted under 35 U.S.C. 154(b) by 133 days.

(21) Appl. No.: 13/506,160

(22) Filed: Mar. 30, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

(56) References Cited

U.S. PATENT DOCUMENTS

PP14,699 P2 * 4/2004 Dufresne ..... Plt./226

* cited by examiner

*Primary Examiner* — Wendy C Haas
(74) *Attorney, Agent, or Firm* — Cassandra Bright

(57) ABSTRACT

A new and distinct *Salvia* cultivar named 'EGGBEN004' is disclosed, characterized by a dense, bushy plant habit, distinctive dark mauve colored flowers, with a white eye, and a rigid, short inflorescence. The new variety is a *Salvia*, normally produced as an outdoor garden or container plant.

2 Drawing Sheets

Latin name of the genus and species: *Salvia microphylla× greggii.*

Variety denomination: 'EGGBEN004'.

BACKGROUND OF THE INVENTION

The new *Salvia* cultivar is a product of a planned breeding program conducted by the inventor, Howard Bentley, in Wonga Park, Victoria, Australia. The objective of the breeding program was to produce new *Salvia* varieties with denser plant habits, strong garden performance, in a range of flower colors. The cross resulting in this new variety was made during April 2006.

The seed parent is the unpatented, *Salvia microphylla* 'Trewithin'. The pollen parent is the unpatented, proprietary variety *Salvia greggii* '005'. The new variety was identified as a potentially interesting selection in October 2006, at a research greenhouse in Wonga Park, Australia. Further observations and evaluations were made during 2007.

Asexual reproduction of the new cultivar 'EGGBEN004' by vegetative cuttings was first performed during 2007, at a research greenhouse in Wonga Park, Australia. Subsequent propagation has shown that the unique features of this cultivar are stable and reproduced true to type on successive generations.

SUMMARY OF THE INVENTION

The cultivar 'EGGBEN004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EGGBEN004' These characteristics in combination distinguish 'EGGBEN004' as a new and distinct *Salvia* cultivar:

1. Bushy plant habit.
2. Dark mauve colored flowers, with a distinctive white eye.
3. Dark calyx coloration.

4. Strong, rigid inflorescence.
5. Dense plant habit.

PARENT COMPARISON

Plants of the new cultivar 'EGGBEN004' are similar to plants of the seed parent, *Salvia microphylla* 'Trewithin' in most horticultural characteristics, however, plants of the new cultivar 'EGGBEN004' are denser, with a less upright plant habit. Additionally, calyx coloration of the parent variety is not as dark as that of the new cultivar.

Plants of the new cultivar 'EGGBEN004' are similar to plants of the pollen parent, *Salvia greggii* '005' in most horticultural characteristics, however, plants of the new cultivar 'EGGBEN004' produce dark mauve colored flowers, with a white eye, whereas the pollen parent produces solid red flowers.

COMMERCIAL COMPARISON

Plants of the new cultivar are best compared to the commercial variety *Salvia gregii* 'Navajo Rose', U.S. Plant Pat. No. 14,699. Plants of the new variety produce different colored flower, with a distinctive white eye not found on this comparator. Plants of 'EGGBEN004' tolerate humid conditions better than the comparator. Additionally, the varieties differ in leaf shape.

BRIEF DESCRIPTION OF THE PHOTOGRAPHS

Figure 1:
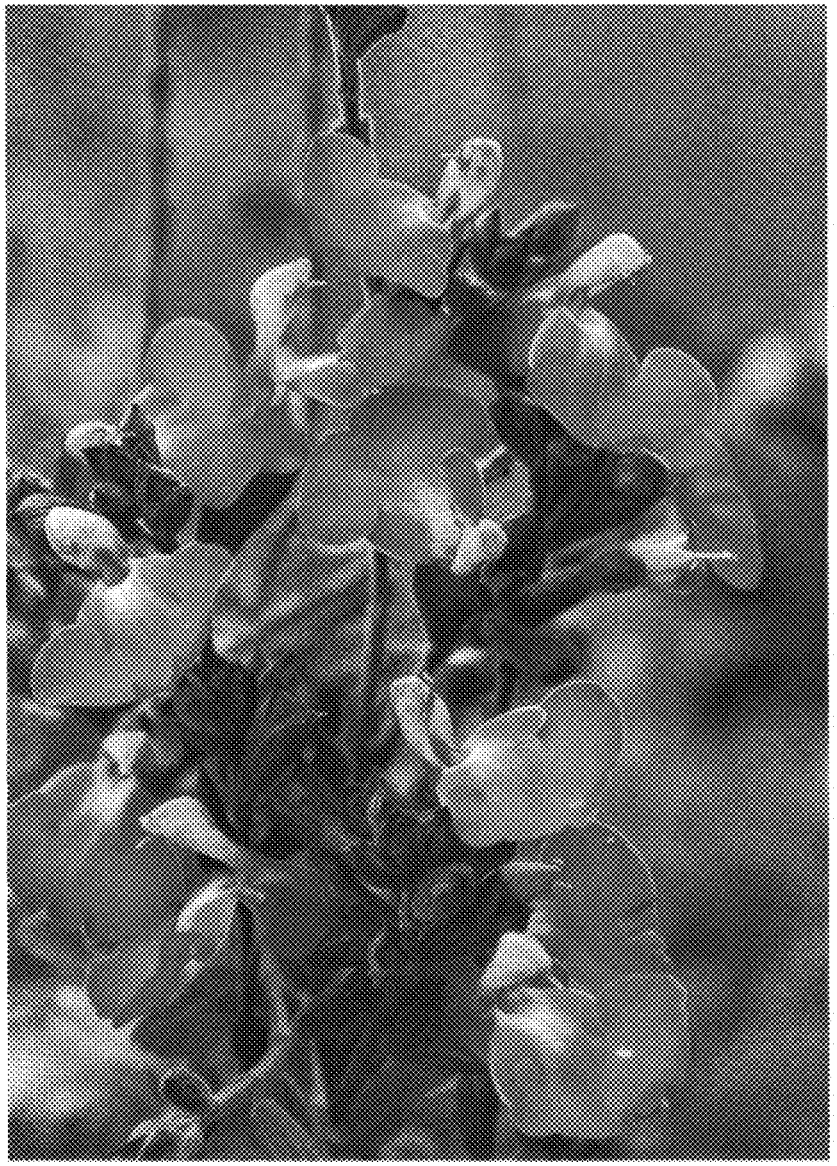

The accompanying photograph in FIG. 1 illustrates in full color a typical flower of 'EGGBEN004'.

Figure 2:
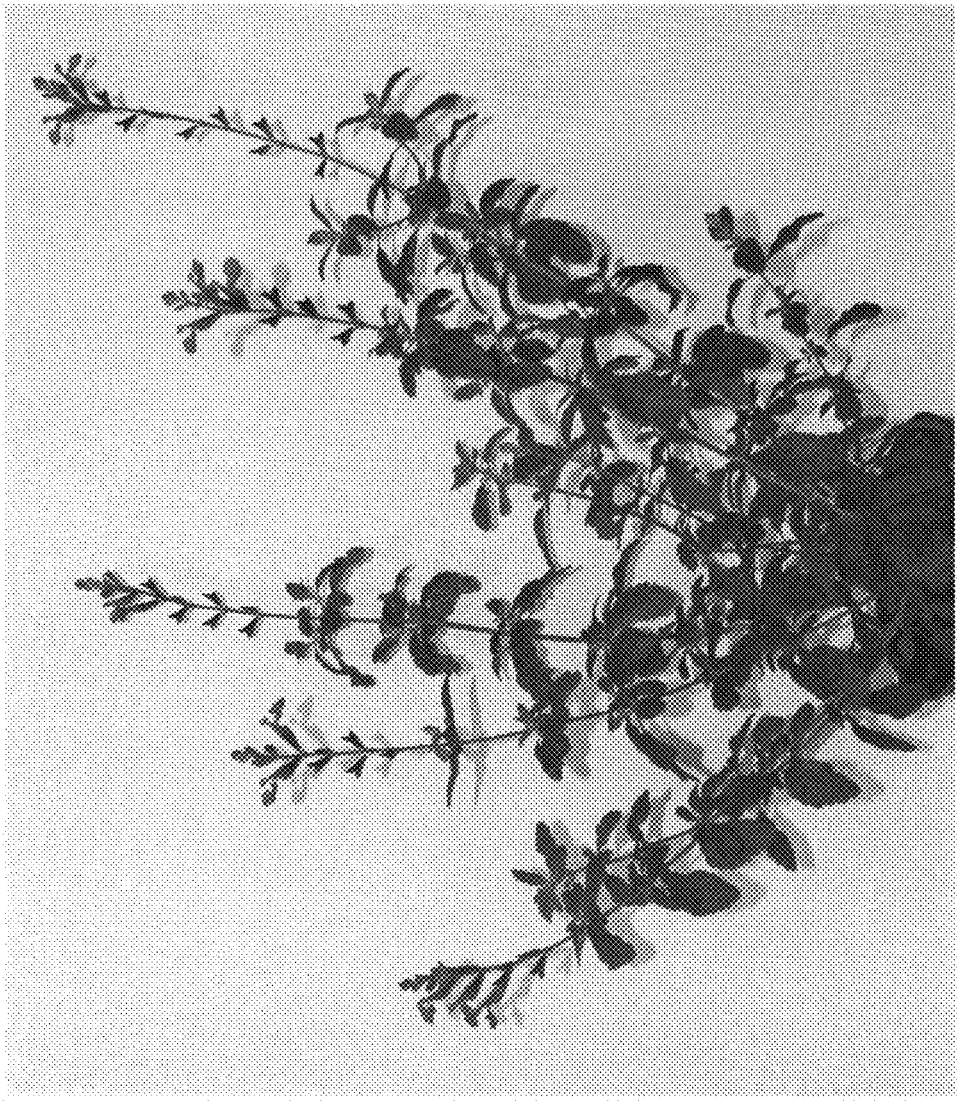

FIG. 2 illustrates in full color a typical plant of 'EGGBEN004' grown in a greenhouse, in Watsonville, Calif., in a commercial 8 inch container.

Age of the plant photographed is approximately 20 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007, Edition, except where general terms of ordinary dictionary significance are used. The following observations and measurements describe 'EGGBEN004' plants grown in a greenhouse in Watsonville, Calif. The growing temperature ranged from 10° C. to 28° C. The greenhouse is un-shaded, giving bright, normal sunlight conditions. Measurements and numerical values represent averages of typical plant types.

Botanical classification: *Salvia microphyllaxgreggii* cultivar 'EGGBEN004'.

PROPAGATION

Time to initiate roots: About 5-8 days at approximately 25° C.

Root description: Fine, densely fibrous.

Time to produce a rooted cutting: About 21 days at 25° C.

PLANT

Growth habit: Outwardly arching annual.

Pot size of plant described: 8 inch pot.

Height: Approximately 38 cm to top of foliage. Approximately 52 cm to top of flowering plane. Measured from soil level of pot.

Plant spread: Approximately 50 cm.

Growth rate: Rapid.

Branching characteristics: Free-branching, Approximately 8 to 10 primary branches.

Length of primary lateral branches: Approximately 35 cm.

Diameter of lateral branches: Approximately 0.4 cm.

Quantity of lateral branches: About 12 to 18.

Stem:

*Color.*—Near RHS Yellow-Green 144A.

*Pubescence.*—Minute pubescence.

Internode length: Approximately 3.0 to 5.0 cm.

Age of plant described: Approximately 20 weeks from an unrooted cutting.

FOLIAGE

Leaf:

*Arrangement.*—Opposite.

*Quantity.*—Approximately 16 fully expanded per main branch.

*Average length.*—Approximately 6.2 cm., including petiole.

*Average width.*—Approximately 3.0 cm.

*Shape of blade.*—Obovate.

*Apex.*—Obtuse.

*Base.*—Obtuse to nearly truncate.

*Attachment.*—Stalked.

*Margin.*—Crenate.

*Texture of top surface.*—Matte, minute, coarse pubescence.

*Texture of bottom surface.*—Matte, minute, coarse pubescence.

*Color.*—Young foliage upper side: Near RHS Green 137A. Young foliage under side: Near RHS Green 137C. Mature foliage upper side: Near RHS Green 137A. Mature foliage under side: Near RHS Green 138A.

*Venation.*—Type: Pinnate. Venation color upper side: Near RHS Green 143C. Venation color under side: Near RHS Green 143C.

*Petiole.*—Average Length: Approximately 1.4 cm. Diameter: Approximately 0.1 cm. Color: Near Green 143C.

FLOWER

Natural flowering season: Flowering from early Spring through late Summer.

Inflorescence type and habit: Flowers arranged in verticillasters on spikes.

Flower longevity on plant: Individual flowers last approximately 1 week on the plant. Each spike lasts approximately 7 weeks with flowers.

Quantity of flowers: About 8 buds and 6 fully opened flowers per spike, at one time. Mature plants have approximately 8 to 14 spikes.

Spike size:

*Diameter.*—Approximately 6.0 cm.

*Height.*—Approximately 10 cm.

Individual flowers:

*Size.*—Diameter: Approximately 1.6 cm. Length: Approximately 2.8 cm.

*Persistence.*—Non-persistent.

*Fragrance.*—Strong, typical *Salvia* scent.

Corolla:

*Petal arrangement.*—The corolla is sympetalous and typically bilabiate with 2 small, highly fused lobes forming an upper lip and 3 larger highly fused lobes forming a lower lip.

*Margin.*—Nearly entire, slightly scalloped.

*Tip shape.*—Upper lip tip retuse, lower lip tip rounded with scallops.

*Length.*—Upper lip Approximately 1.0 cm, lower lip Approximately 1.5 cm. Tube length Approximately 1.7 cm.

*Width.*—Upper lip Approximately 0.4 cm, lower lip Approximately 1.7 cm. Tube width Approximately 0.7 cm.

*Texture.*—Upper lip: Pubescent on exterior surface. Interior surface glabrous. Lower lip: Glabrous all surfaces. Tube: Glabrous.

Color:

*Upper lip.*—When opening: Inner surface: Near RHS Red-Purple 73D. Outer surface: Near RHS Red-Purple 70A. Fully opened: Inner surface: Near RHS Purple 75D. Outer surface: Near RHS Red-Purple 72A. Fading: Inner surface: Near RHS Purple 75D. Outer surface: Near RHS Red-Purple 72A.

Color:

*Lower lip.*—When opening: Inner surface: Near RHS Red-Purple 71C, base White N155D. Outer surface: Near RHS Red-Purple 71B base White N155D. Fully opened: Inner surface: Near RHS Red-Purple 71C, base White N155D. Outer surface: Near RHS Red-Purple 71C, base White N155D. Fading: Inner surface: Near RHS Red-Purple N74D, base White N155D. Outer surface: Near RHS Red-Purple N74D, base White N155D.

Color:

*Tube.*—When opening: Inner surface: Near RHS Purple 75C, opening near White N155D. Outer surface: Near RHS Red-Purple N74C. Fully opened: Inner surface: Near RHS Purple 75C, opening near White N155D. Outer surface: Near RHS Purple 75A. Fading: Inner surface: Near RHS Red-Purple 72A, opening near White N155D. Outer surface: Near RHS Red-Purple 72A.

Bud:

*Shape.*—Ovoid.
*Length.*—Approximately 1.7 cm.
*Diameter.*—Approximately 0.7 cm.
*Color.*—Near RHS Red-Purple 72B.

Calyx:

*Length.*—Approximately 1.7 cm.
*Diameter.*—Approximately 0.8 cm.
*Shape.*—Tubular.
*Sepals.*—Shape: Quantity per flower: 3, fused to form a tube. Unfused Apex: Length: Approximately 0.3 cm. Width: Approximately 0.6 cm. Margin: Entire. Apex: Acute. Texture: Pubescent. Color: Immature: Near RHS Green 137A. Mature: Near RHS Green 137A with strong flush near Greyed-Purple N186A.

Peduncle:

*Length.*—Average 6.0 cm.
*Diameter.*—0.4 cm. Color: Near RHS Green 137A.
*Orientation.*—Upright, straight.
*Strength.*—Strong.
*Texture.*—Pubescent.

Pedicels:

*Length.*—Average 0.4 cm.
*Diameter.*—0.1 cm. Color: Near RHS Green Greyed-Purple N187A.
*Orientation.*—Straight, approximately 45 degree angle from attachment.
*Strength.*—Flexible.
*Texture.*—Pubescent.

REPRODUCTIVE ORGANS

Stamens:

*Number.*—2.
*Filament length.*—Approximately 1.5, approximately 0.7 cm of length fused to petal.
*Filament color.*—Near RHS White N155B, flushed Red-Purple 72B.

Anthers:

*Shape.*—Very narrowly elliptic.
*Length.*—Approximately 2 mm.
*Color.*—Near RHS Greyed-Yellow 161A.
*Pollen.*—Scant colored near Greyed-Orange 167A.

Pistil:

*Number.*—1.
*Length.*—Approximately 2.5 cm.
*Style.*—Length: Approximately 2.1 cm. Color: Near RHS White N155B.
*Stigma.*—Shape: Linear, curled. Color: Near RHS Red-Purple72A. Ovary color: Near RHS Yellow-Green 144C.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'EGGBEN004' as herein illustrated and described.

* * * * *